United States Patent [19]

Anderson et al.

[11] 4,279,903
[45] Jul. 21, 1981

[54] DIPHYDROTHIAZINE DERIVATIVES

[75] Inventors: Martin Anderson, Whitstable; Roger E. Woodall, Sittingbourne, both of England

[73] Assignee: Shell Oil Company, Houston, Tex.

[21] Appl. No.: 151,569

[22] Filed: May 20, 1980

[30] Foreign Application Priority Data

May 23, 1979 [GB] United Kingdom ............... 17981/79
Apr. 17, 1980 [EP] European Pat. Off. ......... 80200351.7

[51] Int. Cl.$^3$ .................... A01N 43/86; C07D 279/06
[52] U.S. Cl. ...................................... 424/246; 544/54; 549/77; 260/347.4
[58] Field of Search ........................... 544/54; 424/246

[56] References Cited

U.S. PATENT DOCUMENTS

| | | | |
|---|---|---|---|
| 3,390,148 | 6/1968 | Austin et al. ........................ 260/240 |
| 3,458,633 | 7/1969 | Austin et al. ........................ 424/246 |
| 3,624,217 | 11/1971 | Koch .................................... 424/246 |
| 4,024,254 | 5/1977 | Roman ............................. 544/54 X |
| 4,033,953 | 7/1977 | Tieman .............................. 544/54 |

FOREIGN PATENT DOCUMENTS 684437 1/1967 Belgium .

OTHER PUBLICATIONS

Kompis, et al., Helvetica Chimica Acta, 60, (1977), pp. 618-628.
Popp, J. Org. Chem., 25, (1960), pp. 646-647.
McFarlan, et al, J. Med. Chem., 13, (1970), pp. 113 and 116-119.
Austin, et al., J. Med. Chem., 15, (1972), pp. 281-285.

*Primary Examiner*—Joseph Paul Brust

[57] ABSTRACT

Certain dihydrothiazine derivatives, useful as anthelmintics and insecticides.

6 Claims, No Drawings

# DIHYDROTHIAZINE DERIVATIVES

BACKGROUND OF THE INVENTION

Certain dihydrothiazines have been found to be active as anthelmintics and as insecticides. These dihydrothiazines are described by the formula:

$$\begin{array}{c} \text{N} \quad \text{H} \\ \phantom{\text{S}}\rangle\!\!-\!\!\overset{|}{\underset{|}{\text{C}}}\!-\!\text{CH}_2\!-\!\text{R} \\ \text{S} \quad \overset{\text{C}-\text{O}-\text{R}^1}{\underset{\text{O}}{\|}} \end{array} \quad (I)$$

wherein R is a thienyl or furyl moiety, or one of these substituted by alkyl, and $R^1$ contains from one to ten carbon atoms, and is an alkyl, alkenyl or alkynyl, cycloalkyl or cycloalkylalkyl, moiety, or one of these substituted by one or more of alkoxy and halogen, or is phenyl or benzyl, or one of these substituted by one or more of alkyl, alkoxy, halogen, haloalkyl, amino, alkylamino, dialkylamino, and nitro. Suitably, the defined aliphatic moieties are of either straight-chain or branched-chain configuration.

The compounds of Formula I usually exist as equilibrium mixtures with their tautomers of the formula:

$$\begin{array}{c} \text{H} \\ \overset{|}{\text{N}} \\ \phantom{\text{S}}\rangle\!\!=\!\!\overset{|}{\underset{|}{\text{C}}}\!-\!\text{CH}_2\!-\!\text{R} \\ \text{S} \quad \overset{\text{C}-\text{O}-\text{R}^1}{\underset{\text{O}}{\|}} \end{array} \quad (II)$$

Usually, one or other of the tautomeric forms will predominate, possibly to the virtual exclusion of the other form, depending upon the nature of the R and $R^1$ groups and the environment of the compounds (e.g., whether the compound is isolated in pure form, or as an acid-addition salt, or is in solution). The present invention extends to the individual tautomeric forms and to mixtures thereof. For brevity, the compounds of the invention are defined in terms of Formula I, the definition being intended to include the tautomeric form defined in Formula II.

Compounds of Formula I form acid-addition salts. The invention includes the pharmacologically acceptable acid-addition salts, such as those of hydrohalic acids, particularly hydrochloric and hydrobromic acids, and acetic, succinic, maleic, fumaric, propionic, citric, lactic, pamoic, tartaric, sulfuric and phosphoric acids.

Preferably, $R^1$ represents alkyl of from one to six carbon atoms, cycloalkyl of from three to six carbon atoms or cycloalkylalkyl of from four to seven carbon atoms and R is 2-furyl, 2-thienyl or either substituted by one or more alkyl moieties of from one to four carbon atoms, particularly methyl.

The most active compounds appear to be those wherein $R^1$ is alkyl of from one to four carbon atoms, or cyclopropylmethyl and R is 2-thienyl or 3-methyl-2-thienyl.

The compounds of Formula I can be prepared by treating a compound of the formula $$\begin{array}{c} \text{CN} \\ \overset{|}{\text{CH}}\!-\!\text{CH}_2\!-\!\text{R} \\ \overset{|}{\text{COOR}^1} \end{array} \quad (III)$$

with 3-aminopropanethiol to give a compound of Formula I, optionally followed by exchanging the moiety $R^1$ for another moiety $R^1$.

The treatment of the compound of Formula III with 3-aminopropanethiol is advantageously carried out at elevated temperature in an inert solvent under an inert gas, such as nitrogen. For example, the reaction may be carried out in methylene chloride, at reflux temperature. If the 3-aminopropanethiol is initially in the form of an acid-addition salt, such as the hydrochloride, the reaction is desirably carried out in the presence of an organic base such as triethylamine.

The optional ester exchange reaction whereby one $R^1$ moiety is substituted for a different $R^1$ moiety may in general be effected by dissolving potassium metal in the appropriate hydroxy compound $R^1$—OH, advantageously in the presence of an inert solvent such as toluene, and adding to the resulting mixture the compound of Formula I (e.g. wherein $R^1$ is methyl) and an appropriate molecular sieve (e.g. size 4A when the $R^1$ group to be removed is methyl). The resulting suspension is heated, conveniently at reflux temperature, and the molecular sieve is subsequently removed by filtration.

The intermediates of Formula III may be prepared by reduction of compounds of the formula $$\begin{array}{c} \text{CN} \\ \overset{|}{\text{C}}\!=\!\text{CH}\!-\!\text{R} \\ \overset{|}{\text{COOR}^1} \end{array} \quad (IV)$$

The reduction is conveniently effected using sodium borohydride similarly to the method of Kompis and Schonholzer, Helv. Chim. Acta, 1977, 60, 618. However, in suitable cases, e.g. when R is thienyl or alkylthienyl, catalytic hydrogenation, using, for example, palladium on charcoal as catalyst, may be employed.

The compounds of Formula IV may be prepared by Knoevenagel condensation of the appropriate aromatic aldehyde of the formula $$\text{R}-\text{CHO} \quad (V)$$

with the appropriate cyanoacetic ester of the formula $$\text{NC}-\text{CH}_2-\text{COOR}^1 \quad (VI)$$

under conditions similar to those described by Popp, J. Org. Chem., 1960, 25, 646.

Dihydrothiazine derivatives of Formula I have utility as anthelmintics and as insecticides. They have low mammalian toxicity.

Accordingly, the invention also provides an anthelmintic or insecticidal composition comprising, as active ingredient, a compound of Formula I in association with a non-toxic carrier therefor. The invention further provides anthelmintic and insecticidal compositions which comprise a compound of Formula I in association with a non-toxic carrier therefor. Also provided in accordance with the invention is the use of a compound of Formula I as an anthelmintic or as an insecticide.

Further in accordance with the invention there is provided a method of combating parasitic worms which comprises subjecting the parasitic worms to exposure to an anthelmintically-effective dose of a compound of Formula I. The method has particular applicability when the parasitic worms are present in the alimentary tract of an animal and the Formula I compound is orally administered to the animal, and is particularly effective in combating parasitic worms in ruminants, e.g., sheep, pigs, cattle and goats.

Oral administration of the compound of Formula I may be by any convenient means, e.g. as a drench, by intubation, in the animal's food and water, in a food supplement or in specific formulations such as solutions, suspensions, dispersions, emulsions, tablets, boluses, powders, granules, capsules, syrups and elixirs. Suitable non-toxic carriers are the conventional, inert, pharmaceutically-acceptable carriers such as water, edible oils, gelatin, lactose, starch, magnesium stearate, talc or vegetable gum.

The dosage of the Formula I compound needed to combat parasitic worms will depend on the particular compound used and the animal being treated. However, in general, the compound will be administered in a dosage of from about 5 to about 200 milligrams per kilogram of the animal's body weight, typically from 10 to 30 milligrams per kilogram for sheep, pigs, goats and cattle. The compound can be administered in a single dose or in a series of doses in a day, or series of days. For any particular animal, a specified dosage regimen should be adjusted according to the individual need, the particular compound used and the professional judgment of the person administering or supervising administration of the compound.

The invention additionally provides a method of combating pests, such as insect pests, at a locus which comprises applying to that locus a pesticidally-effective amount of a compound of Formula I.

A carrier in a pesticidal composition of the invention may be a solid or a liquid, including a material which is normally gaseous but which has been compressed to form a liquid, inorganic or organic, and of synthetic or natural origin. The active ingredient is suitably formulated with at least one carrier to facilitate its application to the locus, for example, plants, seeds or soil, to be treated, or to facilitate storage, transport or handling.

Preferably, a pesticidal composition of the invention contains at least two carriers, at least one of which is a surface-active agent. The surface-active agent may be an emulsifier, a dispersing agent or a wetting agent; it may be non-ionic or ionic. Pesticidal compositions are generally formulated and transported in a concentrated form which is subsequently diluted by the farmer or other user before application. A surface-active agent facilitates this process of dilution.

Any of the carriers commonly used in the formulation of pesticides may be used in pesticidal compositions of the invention, and suitable examples of these are to be found, for example, in British Pat. No. 1,232,930.

Pesticidal compositions of the invention may, for example, be formulated as a wettable powder, microcapsules, a dust, granules, a solution, an emulsifiable concentrate, an emulsion, a suspension concentrate or an aerosol. The pesticidal composition may have controlled release properties, or may be suitable for use as a bait.

Wettable powders usually contain 25, 50 or 75%w of active ingredient and may contain, in addition to inert solid material, 3-10%w of a dispersing agent and, where necessary, 0-10%w of a stabilizer, a penetrant and/or a sticker. A dust is usually formulated as a dust concentrate having a composition similar to that of a wettable powder but without a dispersant, and is diluted in the field with further solid carrier to give a composition usually containing 0.5-10%w of active ingredient.

Granules usually have a size in the range of from 10 to 100 BS mesh (1.676-0.152 mm) and may be manufactured by agglomeration or impregnation techniques. Generally, granules will contain 0.5-25%w active ingredient and 0-10%w of additives, for example, a stabilizer, slow release modifier and/or a binding agent.

Emulsifiable concentrates usually contain, in addition to a solvent, and, when necessary, co-solvent, 10-50% w/v active ingredient, 2-20% w/v emulsifier and 0-20% w/v of other additives, for example, a stabilizer, a penetrant and/or a corrosion inhibitor. A suspension concentrate is a stable, non-sedimenting, flowable product and usually contains 10-75%w active ingredient, 0.5-15%w of dispersing agent, 0.1-10%w of suspending agent, for example, protective colloid and/or a thixotropic agent, and 0-10%w of other additives including, for example, a defoamer, a corrosion inhibitor, a stabilizer, a penetrant and/or a sticker, and as dispersant, water or an organic liquid in which the active ingredient is substantially insoluble; certain organic additives and/or inorganic salts may be dissolved in the dispersant to assist in preventing sedimentation or as anti-freeze for water.

The aqueous dispersions and emulsions formed by diluting a wettable powder or an emulsifiable concentrate of the invention with water, also lie within the scope of the present invention. Such dispersions and emulsions may be of the water-in-oil or of the oil-in-water type, and may have a thick 37 mayonnaise"-like consistency.

A pesticidal composition of the invention may also contain other ingredients, for example, one or more other compounds possessing pesticidal, herbicidal or fungicidal properties, or attractants, for example, pheromones or food ingredients, for use in baits and trap formulations.

The invention will be better understood from the following illustrative Examples, of which Examples 9 to 15 and 18 relate to the preparation of compounds of the invention and Examples 1 to 8, 16 and 17 relate to intermediates. In all cases, the identity of the product involved was confirmed by appropriate chemical and spectral analyses.

Example 1—Methyl 2-cyano-3-(2-thienyl)acrylate (1)

A solution of 1.0 ml of piperidine in 10 ml of dioxane was added carefully to a stirred solution of 33.65 g thiophene-2-carboxaldehyde and 29.7 g of methyl cyanoacetate in 40 ml of dioxane. On standing the reaction mixture overnight at room temperature a crystalline precipitate was obtained which was filtered off, washed with cold dioxane and dried in vacuo to give 1, as a solid, mp 104°–106° C.

EXAMPLES 2 TO 4

By methods similar to that of Example 1, there were prepared the following compounds:
 ethyl 2-cyano-3-(2-thienyl)acrylate (2), mp 94°–95° C.
 t-butyl 2-cyano-3-(2-thienyl)acrylate (3), mp 114°–115° C.
 methyl 2-cyano-3-(3-methylthien-2-yl)acrylate (4), mp 135°–136°0 C.

EXAMPLE 5—Methyl 2-cyano-3-(2-thienyl)propionate (5)

29 g of methyl 2-cyano-3-(2-thienyl)acrylate was dissolved in 300 ml of methanol/water (80:20 v/v). To the resulting solution was added 3 drops of molar aqueous sodium hydroxide solution followed by 1.8 g of sodium borohydride and the suspension thus formed was stirred overnight at room temperature. The reaction mixture was then neutralized using molar aqueous acetic acid solution and volatile components were evaporated off under reduced pressure. The residue was suspended in water and extracted with toluene. The extract was dried over sodium sulfate and the toluene was evaporated off in vacuo to give a crude product which was purified by distillation to give 5, as a liquid, bp 172° C. (12 Torr.).

EXAMPLES 6 AND 7

By methods similar to that of Example 5 there were also prepared:
 ethyl 2-cyano-3-(2-thienyl)propionate (6), a liquid, bp 112°–114° C. (0.25 Torr.)
 t-butyl 2-cyano-3-(2-thienyl)propionate (7), an oil

EXAMPLE 8—Methyl 2-cyano-3-(3-methylthien-2-yl)propionate (8)

75.0 g of methyl 2-cyano-3-(3-methylthien-2-yl)acrylate was suspended in 1 liter of methanol and hydrogenated in four batches in a Parr apparatus at 50° C. and 4.23 atmospheres hydrogen pressure, using 0.25 g of 10% palladium/charcoal catalyst per batch. Distillation of the residue remaining after removal of the catalyst and solvent gave 8, as a pale yellow oil, bp 119° C. (0.5 Torr.).

EXAMPLE 9—Methyl 2-(5,6-dihydro-4H-1,3-thiazin-2-yl)-3-(2-thienyl)-propionate (9)

A suspension of 4.7 g of 3-aminopropanethiol hydrochloride in 150 ml of methylene chloride containing 6.5 g of methyl 2-cyano-3-(2-thienyl)propionate and 3.7 g of triethylamine was stirred at reflux temperature under nitrogen for 17 hours. After filtering of the reaction mixture the solvent was evaporated off under reduced pressure, leaving an oily residue which was suspended in water and extracted with ether. The ether extract was dried over sodium sulfate, the other ether was evaporated off, and the residue was distilled under reduced pressure to give 9, as a pale yellow liquid, bp 171° C. (0.4 Torr.).

EXAMPLES 10 TO 12

The following compounds were prepared by methods similar to that used in Example 9:
 ethyl 2-(5,6-dihydro-4H-1,3-thiazin-2-yl)-3-(2-thienyl)propionate (10), a liquid, bp 144°–154° C. (0.2 Torr.)
 t-butyl 2-(5,6-dihydro-4H-1,3-thiazin-2-yl)-3-(2-thienyl)propionate (11), an oil
 methyl 2-(5,6-dihydro-4H-1,3-thiazin-2yl)-3-(3-methylthien-2-yl)propionate (12), a liquid, bp 163°–164° C. (0.4 Torr.)

EXAMPLE 13—n-propyl 2-(5,6-dihydro-4H-1,3-thiazin-2-yl)-3-(2-thienyl)-propionate (13)

1.0 g of potassium was dissolved in 6.0 g of n-propanol and the solution was diluted with 75 ml of dry toluene. To the resulting solution was added 5.4 g of (9) and 30 g of size 4A molecular sieve (BDH reagent grade), which had previously been stored at 300° C. The resulting suspension was stirred vigorously at reflux temperature for 16 hours. After removal of the molecular sieve the solvent components were evaporated off under reduced pressure. The residue was subjected to chromatography on a silica gel column using diethyl ether as eluent to give 13, as an oil.

EXAMPLES 14 AND 15

The following compounds were prepared by methods similar to that of Example 13.
 n-butyl 2-(5,6-dihydro-4H-1,3-thiazin-2-yl)-3-(2-thienyl)-propionate (14), an oil
 cyclopropylmethyl 2-(5,6-dihydro-4H-1,3-thiazin-2-yl)-3-(2-thienyl)propionate (15), an oil

EXAMPLE 16—Methyl 2-cyano-3-(2-furyl)acrylate (16)

A solution of 1.0 ml of piperidine in 10.0 ml of dioxane was added carefully to a stirred solution of 28.8 g of furfural and 29.7 g of methyl cyanoacetate in 40 ml of dioxane. After stirring at room temperature overnight, the reaction mixture was diluted with 100 ml of water and extracted with toluene. The extract was dried over sodium sulfate and the toluene was evaporated under reduced pressure to give a crude product as a red solid. The crude product was crystallized from toluene/hexane to give 16, as red crystals, mp 90°–91° C.

EXAMPLE 17—Methyl 2-cyano-3-(2-furyl)propionate (17)

26.4 of of methyl 2-cyano-3-(2-furyl)acrylate was dissolved in 300 ml of methanol/water (80:20 v/v). Three drops of molar aqueous sodium hydroxide were added to the resulting solution, followed by 1.8 g of sodium borohydride. The suspension thus formed was stirred at room temperature overnight and was then neutralized with molar aqueous acetic acid. Volatile components of the reaction mixture were evaporated off under reduced pressure and the residue was suspended in water and extracted with toluene. The extract was dried over sodium sulfate and the toluene was evaporated off under reduced pressure to give a crude product as a red oil. The red oil was partially purified by chromatography on silica gel using toluene/methanol (9:1 v/v) as eluent and the partially purified material therefrom was distilled under reduced pressure to give 17, as a pale yellow liquid, bp 82° C. (0.2 Torr.).

EXAMPLE 18—Methyl 2-(5,6-dihydro-4H-1,3-thiazin-2-yl)-3-(2-furyl)-propionate (18)

A suspension of 7.33 g of 3-aminopropanethiol hydrochloride in 100 ml of dry methylene chloride containing 10.1 g of methyl-2-cyano-3-(2-furyl)propionate and 5.8 g of triethylamine was stirred at reflux temperature under nitrogen for 17 hours. After filtering of the reaction mixture, the solvent was evaporated off under reduced pressure, leaving an oily residue which was suspended in water and extracted with ether. The ether extract was dried over sodium sulfate, the ether was evaporated off, and the residue was distilled under reduced pressure to give 18, as a pale yellow liquid, bp 158° C. (0.4 Torr.).

The parasiticidal and pesticidal activity of the compounds of the invention was determined by the following tests.

Test 1

The compounds were tested in an anthelmintic screen which was found to have a high specificity for ruminant-related nematodes and to detect known ruminant anthelmintics. The screen involved determining the efficacy of the compounds in treating rats infested with rat roundown (*Nippostrongylus brasiliensis*).

White, male, Sprague-Dawley-derived rats having a body weight of approximately 50 grams were exposed to *N. brasiliensis* infection by inoculation by subcutaneous injection in the cervical region with 1 milliliter of water containing about 200 *N. brasiliensis* larve. The rats were then held for 9 days for maturation of the infection.

Each test compound was weighed in 50 milligram amounts into glass vials with screw caps. When prepared for testing, the test compound was triturated in a mortar and 6 milliliters corn oil added as a vehicle. If a test compound would not suspend well or go into solution in the corn oil when triturated in the mortar, the mixture was subjected to ultrasonic oscillation and the associated heat, which generally accomplished the desired effect. Following the formulation of the test compound in the corn oil vehicle, the mixture was incorporated into 200 grams of ground rat chow. Using round-bottom bowls and a hand-held electric mixer, the test compound, corn oil, and feed were well mixed. The medicated feed then was transferred to labeled plastic bags for filling feeders.

On the ninth day following exposure to the parasitic infection, rats were randomly distributed to plastic holding boxes. Two rats were used as a treatment group for each of a series of different dose rates of each test compound. Five to ten non-medicated controls also were included. Special self-feeding feeders containing the medicated or non-medicated feeds were then added to each box along with an identification card. Following a 5-day medicated feed treatment period, the rats were transferred to special observation cubicles for a 24-hour fast prior to necropsy. The rats were sacrificed using carbon dioxide. The proximal 10 to 15 inches of the small intestine was removed, compressed under heavy glass plates, and the numbers of small red parasitic worms were counted by eye.

The test results are given in Table I:

TABLE I

| Compound No. | Concentration of Test Compound in Feed (ppm) | Calculated Total Dose of Test Compound per Rat (mg/kg) | No. of Animals Tested | No. of Animals Cleared of Worms | % Reduction in Number of Worms Compared with Control |
|---|---|---|---|---|---|
| 9 | 100 | 60 | 4 | 2 | 96 |
|  | 30 | 18 | 4 | 1 | 60 |
| 10 | 300 | 180 | 2 | 2 | 100 |
|  | 250 | 150 | 2 | 2 | 100 |
|  | 100 | 60 | 2 | 2 | 100 |
|  | 30 | 18 | 2 | 0 | 48 |

TABLE I-continued

| Compound No. | Concentration of Test Compound in Feed (ppm) | Calculated Total Dose of Test Compound per Rat (mg/kg) | No. of Animals Tested | No. of Animals Cleared of Worms | % Reduction in Number of Worms Compared with Control |
|---|---|---|---|---|---|
| 11 | 300 | 180 | 2 | 0 | 98 |
|  | 250 | 150 | 2 | 1 | 79 |
|  | 100 | 60 | 2 | 0 | 48 |
| 12 | 300 | 180 | 2 | 2 | 100 |
|  | 100 | 60 | 2 | 2 | 100 |
|  | 30 | 18 | 2 | 0 | 74 |
| 13 | 250 | 150 | 2 | 2 | 100 |
|  | 100 | 60 | 2 | 2 | 100 |
|  | 30 | 18 | 2 | 0 | 90 |
| 14 | 300 | 180 | 2 | 2 | 100 |
|  | 250 | 150 | 2 | 2 | 100 |
|  | 100 | 60 | 2 | 2 | 100 |
|  | 30 | 18 | 2 | 0 | 43 |
| 15 | 300 | 180 | 2 | 2 | 100 |
|  | 200 | 120 | 2 | 2 | 100 |
|  | 100 | 60 | 2 | 2 | 100 |
|  | 30 | 18 | 2 | 0 | 79 |

Test 2

Compound 12, its tartrate salt, and the tartrate salt of Compound 9, were tested for anthelmintic activity in sheep.

Twenty-three sheep having body weights in the range 25 to 35 kilograms and substantial fecal parasite egg counts (>1000) were randomly assigned to one of three treatment groups of five sheep each, or a control group of eight sheep. Five days prior to administration of the test compound, each group was moved to a respective holding pen where food (Happy Holme Farms, MD Lamb Fattener #3) and water were provided on a free-choice basis.

Based upon pretreatment body weights, individual dosages of the compound of Example 13 at 15 mg/kg, the tartrate salt of the compound of Example 13 at 15 mg/kg, and the tartrate salt of the compound of Example 10 at 25 mg/kg were prepared. The compounds were formulated by adding one drop of Tween 80 emulsifier while mixing the compound with a small volume of water. Where ready mixing did not occur, ultrasonic oscillation was used to disperse the compound. Additional water was added to bring total volume of each dosage to 35 milliliters. The dosages were administered as a single oral drench, control animals being given plain water.

On the fifth day after treatment all the sheep were taken off food following the morning feed. Thirty-six hours later, necropsies were performed for each animal. The abomasum, small intestine and cecum/colon of each sheep were removed and the contents were washed over a 0.25 millimeter screen. The abomasum and small intestine of each sheep were subjected to an artificial digestion overnight, and once again washed over a 0.25 millimeter screen. All washings were placed in a 10% formalin solution, and following conventional procedures, all of the parasites were collected, identified, counted and tabulated, and percentage reductions in infestations of the treated animals were calculated. Results are given in Table II.

TABLE II

| Parasite Species | Compound 12 (15 mg/kg) | Tartrate Salt of Compound 12 (15 mg/kg) | Tartrate Salt of Compound 9 (25 mg/kg) |
|---|---|---|---|
| Haemonchus | 84.9 | 47.6 | 78.2 |
| Ostertagia | 79.0 | 60.4 | 74.3 |
| Trichostrongylus | 97.0 | 93.3 | 98.4 |
| Nematodirus | 98.8 | 91.1 | 99.7 |
| Hookworm | 100 | 100 | 98.8 |
| Chabertia | 59.1 | 79.1 | 84.2 |
| Cooperia | 95.1 | 97.7 | 99.6 |
| Trichuris | 0 | 55.2 | 46.1 |
| Overall | 85.5 | 80.3 | 90.6 |

Test 3

Compound 12, its tartrate salt, and Compound 9 were tested for anthelmintic activity in pigs by the following procedure.

Ten young pigs having body weights in the range of 28 to 48 kilograms and substantial fecal egg counts (>500) were placed in individual pens where they were given a swine grower ration and water ad libitum throughout a three day acclimatization period and four day test period. The pigs were randomly assigned to three treatment groups of two pigs each and a control group of four pigs.

Individual dosages of the test compounds were prepared at 20 mg/kg body weight. Each individual dose of Compound 12 was mixed with an equal weight of corn oil and placed in a hard gelatin capsule which was administered with the use of a balling gun. The tartrate salts of Compound 12 and Compound 9 were formulated by mixing each individual dose with 4 milliliters of corn oil, six drops of Tween 80 emulsifier and 5 milliliters of water, with ultrasonic oscillation to form an emulsion. The individual dosages were administered through a stomach tube. The control pigs received plain water.

The feces passed by each pig were collected thrice daily for four days. Twenty-four hours prior to necropsy the pigs were taken off food. Four days after treatment the pigs were killed and a necropsy was conducted for the collection of all worm parasites remaining in the gastrointestinal tracts. The intestinal contents and fecal collections were washed over 0.42 millimeter screens. Each of the washings was stored in a 10% formalin solution. Each necropsy or fecal washing was inspected for recovery, identification and counting of all worm parasites passed following treatment or remaining at necropsy. Results are given in Table III.

TABLE III

| Parasite Species | Compound 12 (20 mg/kg) | Tartrate Salt of Compound 12 (20 mg/kg) | Compound 9 (20 mg/kg) |
|---|---|---|---|
| Roundworms | 100 | 78 | 100 |
| Whipworms | 0 | 0 | 17 |
| Nodular Worms | 90 | 24 | 94 |

Test 4

The insecticidal activity of compounds of the invention was demonstrated on aphids (*Aphids fabae*) by the following procedure.

Pairs of leaves were removed from broad bean plants and placed on filter paper inside plastic petri dishes. The leaves were sprayed on the undersurface with an aqueous formulation containing 20% by weight of acetone, 0.05% by weight of TRITON X-100 as wetting agent and 0.4% by weight of the compound to be tested. Varying concentrations were obtained by diluting the formulation. After spraying, the leaves were left to dry for 0.5 to 1 hour and each leaf pair was infested with ten adult aphids. After 24 hours the percentages of dead and moribund aphids were recorded.

The concentrations of the test compounds in the formulation that were required to kill approximately 50% of the insects (the $LC_{50}$ dosages) were obtained and are expressed as toxicity grades as follows:

| $LC_{50}$ (% Active Material in Spray) | Toxicity Grade |
|---|---|
| >0.6 | 0 |
| ≦0.6 and >0.2 | 1 |
| ≦0.2 and >0.006 | 2 |
| ≦0.06 and >0.02 | 3 |
| ≦0.02 and >0.006 | 4 |
| ≦0.006 | 5 |

Results of the tests are given in Table IV.

TABLE IV

| Compound | Toxicity Grade on *Aphis fabae* |
|---|---|
| 9 | 3 |
| 10 | 3 |
| 11 | 1 |
| 12 | 2 |
| 13 | 3 |
| 14 | 2 |
| 15 | 2 |
| 18 | 3 |

We claim:

1. A tautomeric compound represented by the formulae:

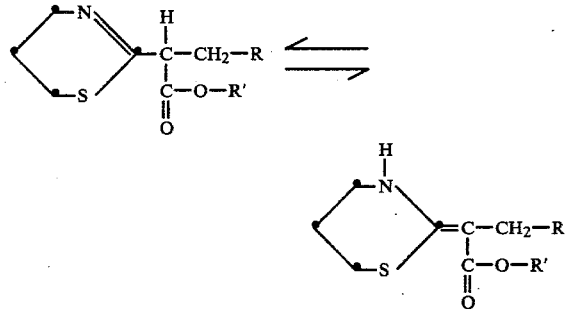

wherein R is thienyl or furyl, or one of these substituted by alkyl of from one to six carbon atoms, and $R^1$ contains from one to ten carbon atoms, and is alkyl, alkenyl, alkynyl, cycloalkyl, or cycloalkylalkyl or one of these substituted by alkoxy or halogen, or is phenyl or benzyl, or one of these substituted by alkyl, alkoxy, halogen, haloalkyl, amino, alkylamino, dialkylamino, or nitro, and the pharmacologically acceptable acid-addition salts thereof.

2. A compound according to claim 1 wherein $R^1$ is alkyl of from one to six carbon atoms, cycloalkyl of from three to six carbon atoms or cycloalkylalkyl of from four to seven carbon atoms and R is 2-furyl, 1-thienyl or either substituted by alkyl of from one to four carbon atoms, and the acid-addition salt is the hydrohalide.

3. A compound according to claim 2 wherein $R^1$ is alkyl of from one to four carbon atoms, or cyclopropylmethyl and R is 2-thienyl or 3-methyl-2-thienyl.

4. A method for controlling helminths in an animal which comprises orally administering to an infested animal an anthelmintically effective dosage of a compound of claim 1.

5. A method for controlling helminths in an animal which comprises orally administering to an infested animal an anthelmintically effective dosage of a compound of claim 2.

6. A method for controlling helminths in an animal which comprises orally administering to an infested animal an anthelmintically effective dosage of a compound of claim 3.

* * * * *

UNITED STATES PATENT AND TRADEMARK OFFICE
CERTIFICATE OF CORRECTION

PATENT NO. : 4,279,903
DATED : July 21, 1981
INVENTOR(S) : Martin Anderson and Roger E. Woodall It is certified that error appears in the above-identified patent and that said Letters Patent are hereby corrected as shown below:

In the title - "Diphydrothiazine" should read
-- Dihydrothiazine --

Column 4, line 36, "37 mayonnaise" should read
-- "mayonnaise" --

Column 5, line 1, "mp 135° - 136°0 C." should read
-- mp 135° - 136° C. --

Column 7, line 20, "larve" should read -- larvae --

Column 10, lines 17-21, "$\leq$" should read -- $<$ --

Column 10, line 65, Claim 2, "1-thienyl" should read
-- 2-thienyl --

Signed and Sealed this

Fourth Day of January 1983

[SEAL]

Attest:

Attesting Officer

GERALD J. MOSSINGHOFF

Commissioner of Patents and Trademarks